(12) United States Patent
Mailland et al.

(10) Patent No.: US 8,303,997 B2
(45) Date of Patent: Nov. 6, 2012

(54) FILM-FORMING LIQUID FORMULATIONS FOR DRUG RELEASE TO HAIR AND SCALP

(75) Inventors: Federico Mailland, Lugano (CH); Emanuela Mura, Como (IT)

(73) Assignee: Polichem SA, Luxembourg (LU)

( * ) Notice: Subject to any disclaimer, the term of this patent is extended or adjusted under 35 U.S.C. 154(b) by 0 days.

(21) Appl. No.: 12/931,583

(22) Filed: Feb. 4, 2011

(65) Prior Publication Data

US 2011/0183016 A1 Jul. 28, 2011

Related U.S. Application Data

(63) Continuation-in-part of application No. PCT/EP2009/059807, filed on Jul. 29, 2009.

(30) Foreign Application Priority Data

Aug. 4, 2008 (EP) .................................... 08161757

(51) Int. Cl.
*A01N 65/00* (2009.01)
(52) U.S. Cl. ....................................................... 424/725
(58) Field of Classification Search .................. None
See application file for complete search history.

(56) References Cited

U.S. PATENT DOCUMENTS

2002/0192280 A1 12/2002 Hunter et al.

FOREIGN PATENT DOCUMENTS

| CN | 1969802 | 5/2007 |
| EP | 1491202 | 12/2004 |
| WO | 02/07683 | 1/2002 |

OTHER PUBLICATIONS

Biruss, et al., "Skin permeation of different steroid hormones from polymeric coated liposomal formulations" European Journal of Pharmaceutics and Biopharmaceutics, vol. 62, No. 2, p. 210-219, Feb. 1, 2006.
International Preliminary Report on Patentability for PCT/EP2009/059807 of Jan. 11, 2011.
International Search Report for PCT/EP2009/059807 of Nov. 12, 2009.
CN1969802 English Language Translation.

*Primary Examiner* — Michael Meller
(74) *Attorney, Agent, or Firm* — Hueschen and Sage

(57) ABSTRACT

The present invention is directed to liquid compositions containing chitosan, a chitosan derivative or a physiologically acceptable salt thereof, which form a film after application onto the scalp and/or the hair, which compositions are useful for delivery of actives onto the scalp surface and/or onto the hair.

28 Claims, 1 Drawing Sheet

Finasteride permeated (mg/cm²) as a mean of 3 experiments.
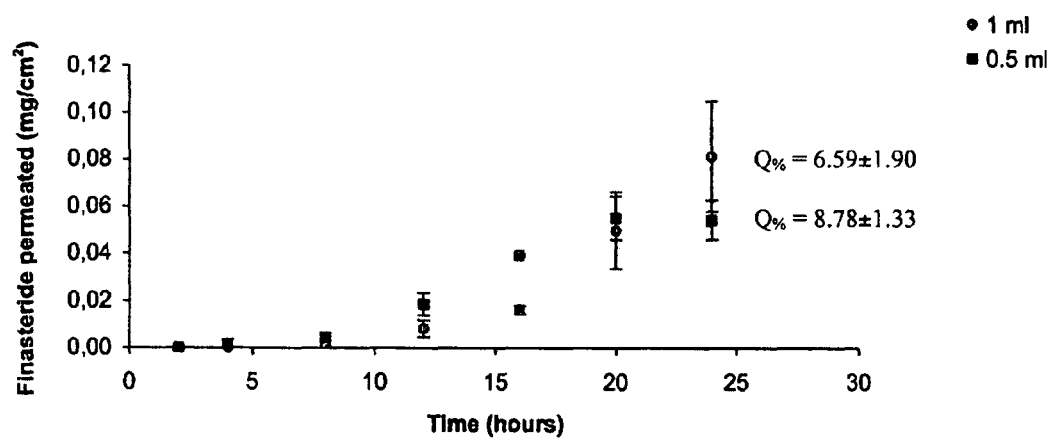

FILM-FORMING LIQUID FORMULATIONS FOR DRUG RELEASE TO HAIR AND SCALP

BACKGROUND OF THE INVENTION

The present invention relates to liquid compositions containing chitosan, a chitosan derivative or a physiologically acceptable salt thereof, for the preparation of a medicament, or a medical device, or a sanitary product, or a cosmetic, which compositions form a film after application onto the scalp, or onto the hair. The film-forming compositions of the invention are useful for the delivery of actives onto the scalp surface and/or onto the hair.

FIELD OF THE INVENTION

The delivery of active ingredients contained in drugs, sanitary products, detergents or cosmetics, to the scalp or the hair often constitutes a problem in that the common formulations, like creams, ointments, gels, powders, or foams, do not allow a long lasting contact with the scalp or hair surface.

Chitosan and its derivatives are amino-polysaccharides, derived from chitin extracted from the exoskeleton of crustaceans, which chitosan and its derivatives are known in the art for their use in different preparations. KR20020084672 discloses chitosan to be an ingredient of microspheres, and is useful as a carrier for separation of proteins or peptides. KR20020048534 reports that chitosan is an ingredient of a pack composition for skin massage, and includes paraffin wax as an effective component. JP2005306746 teaches the use of chitosan as an ingredient of gel-like or spongy preparations of botulinum toxin as a wrinkle therapeutic agent. WO2005055924 reports chitosan derivatives as ingredients of hydrogels useful for cavity-filling wound dressings. JP2004231604 teaches compositions of chitosans having a high deacetylation degree as an ingredient of a carrier sheet with a porous spongy texture. WO03042251 discloses compositions comprising chitosan in the form of a network of nano-sized fibers. WO02057983 discloses a multi-layered, air gap sheet of chitosan with a regular lamellar structure which retains drugs for a prolonged period of time. JP11060605 teaches an amphiphilic chitosan derivative which can be used as a dispersion stabilizer or an emulsifier in a drug for application to skin. Finally, EP1303249, discloses a nail varnish composition containing at least one antimycotic agent and a hydroxyalkyl or a carboxyalkyl chitosan, and WO2004/112814 discloses a nail restructuring composition based on one herb extract from the genus Equisetum in combination with hydroxypropyl chitosan.

It has now surprisingly been found that liquid preparations of chitosan derivatives may form an elastic film after application to the scalp and, after evaporation of the volatile solvents, are suitable to maintain drugs and other actives in intimate contact with the scalp and/or hair surface. The film forming solutions containing chitosans, pharmaceutically active agents and volatile solvents, may easily be sprayed onto the scalp or hair surface, allowing quick evaporation of the volatile solvents and easy formation of an elastic film. The compositions of the invention solve the problem of, for example, the bothersome sensation of oily scalp often experienced with creams, lotions and ointments, and avoid long periods for drying when large scalp surfaces are to be treated. The film forming solutions of chitosan or chitosan derivatives may also be applied on the scalp by gentle massage or by spray.

The film forming solutions of chitosans allow for quick penetration of actives into the deep layers of the scalp, and are, thus, useful for the safe treatment and/or prevention of scalp conditions and/or diseases, like hair loss, where penetration of the active ingredient into the hair follicles is needed. Moreover, the dermal film formed after evaporation of solvents of liquid chitosan compositions allows for prolonged intimate contact with the scalp and/or hair surface, and continuous release of drugs or other actives for many hours after the application.

BRIEF SUMMARY OF THE INVENTION

The object of the present invention is thus represented by a method for the treatment and/or prevention of scalp and/or hair conditions and/or hair diseases comprising applying to the scalp and/or hair of a human being, a composition comprising:

(a) chitosan, a chitosan derivative or a physiologically acceptable salt thereof;

(b) at least a pharmaceutical or a cosmetic active ingredient selected from 5-alpha reductase inhibitors, antiandrogenic hormones, potassium channel agonists, amino acids, plant extracts and antioxidants; and (c) at least one volatile solvent, such a method wherein component (a) is present in an amount of from 0.1 to 10 wt. % based on total weight of the composition, such a method wherein component (a) is present in an amount of from 0.2 to 5 wt. % based on total weight of the composition, such a method wherein component (a) is present in an amount of from 0.25 to 2.0 wt. % based on total weight of the composition, such a method wherein component (a) is a water soluble chitosan derivative or a salt thereof, such a method wherein the water soluble chitosan derivative is a hydroxyalkyl-chitosan, such a method wherein the hydroxyalkyl-chitosan is hydroxypropyl-chitosan, such a method wherein component (b) is present in an amount of from 0.001 to 25 wt. % based on total weight of the composition, such a method wherein component (b) is present in an amount of from 0.2 to 10 wt. % based on total weight of the composition, such a method wherein component (b) is present in an amount of from 0.4 to 5.0 wt. % based on total weight of the composition, such a method wherein the 5-alpha reductase inhibitor is selected from finasteride, dutasteride, azelaic acid, betasitosterol, zinc, and Vitamin B6, such a method wherein the antiandrogenic hormone is selected from spironolactone, ciproterone acetate, flutamide, ketoconazole, estrogens and salts thereof, such a method wherein the potassium channel agonist is minoxidil, such a method wherein the amino acid is selected from L-cysteine, N-acetylcysteine, L-cystine, L-methionine, dimethylsulphone, and L-taurine, such a method wherein the plant extract is selected from extracts of *Serenoa repens, Aloe vera, Equisetum arvense, Panicum miliaceum, Pygeum africanum, Urtica dioica, Coix lachrymal-jobi*, and *Eriobotrya japonica*, such a method wherein the antioxidant is selected from ascorbic acid; glutathione; melatonin; tocopherols and tocotrienols; polyphenolic antioxidants including resveratrol and flavonoids; viniferols; and carotenoids including lycopene, carotenes, such a method wherein component (c) is present in an amount of from 25% to 90 wt. % based on total weight of the composition, such a method wherein component (c) is present in an amount of from 30% to 85 wt. % based on total weight of the composition, such a method wherein component (c) is present in an amount of from 35% to 80 wt. % based on total weight of the composition, such a method wherein component (c) is a lower alkanol, such a method wherein the lower alkanol is selected from ethanol and isopropanol, such a method wherein the composition further comprises water, such a method wherein the composition further comprises customary excipients and/or adjuvants, such a method wherein the composition is in the form of a liquid selected from a solution, emulsion, suspension and colloid, such a method wherein the composition is applied by spraying, such a method wherein the scalp and/or hair conditions and/or diseases are selected from hair loss, baldness, alopecia, androgenetic alopecia and hair fragility, such a method wherein the composition comprises at least one penetration modifying system, such a method wherein the penetration modifying system is selected from diethylene glycol monoethyl ether and microcapsules.

BRIEF DESCRIPTION OF THE DRAWINGS

FIG. 1. Finasteride permeation of rat skin.

DETAILED DESCRIPTION OF THE INVENTION

An object of the present invention is a composition in the form of a liquid formulation containing chitosan, a chitosan derivative or a physiologically acceptable salt thereof, useful for delivery of actives onto the scalp and/or hair. Among chitosan derivatives, hydroxyalkyl chitosans, such as hydroxypropyl chitosan, or other water soluble chitosans are preferred.

The film forming solutions of chitosan are topically applied to the scalp and/or hair of the recipient, preferably a human being; they may be applied by gentle massage onto the scalp, or may easily be sprayed, allowing the formation of an elastic film. The film forming solutions of chitosans allow quick penetration of actives, a long lasting intimate contact of the actives with the scalp and continuous release of drugs for many hours after the application.

The liquid preparations of the instant invention are in the form of solutions, emulsions, colloids or suspensions, comprising chitosan or a chitosan derivative from 0.1 to 10 wt. % (percentages by weight are given with respect to the whole preparation), from 0.2 to 5 wt. %, including from 0.25 to 2.0 wt. %, and at least one active pharmaceutical or cosmetic agent, or a plant extract, in an amount of from 0.001 to 25 wt. %, from 0.2 to 10 wt. %, including from 0.4 to 5.0 wt. %, as well as at least one volatile solvent in an amount of from 25 to 90 wt. %, from 30 to 85 wt. %, or from 35 to 80 wt. %. The compositions of the invention are suitable to form an elastic film after evaporation of solvent, said film being in intimate contact with the scalp surface and/or of the hair, thereby providing rapid and long lasting penetration of said actives which is useful for treating scalp and/or hair conditions and/ or diseases, like hair loss, baldness, alopecia, androgenetic alopecia, hair fragility and other hair conditions.

The compositions of the instant invention are superior to conventional formulations, in that they can be sprayed onto the surface of the skin and/or hair, leaving a uniform and invisible film. Moreover, the compositions according to the present invention do not dirty, do not dry like gels and lotions, and do not give a bothersome sensation when applied as do other rigid film preparations.

The pharmaceutical compositions are prepared according to conventional techniques, using compatible excipients and pharmaceutically acceptable carriers, and may contain, in combination, other active principles with complementary and/or other activities.

The compositions prepared according to the present invention may be in the form of solutions, emulsions, suspensions and colloids. The compositions according to the invention may be applied onto a hairless or hairy scalp surface by gentle massage of the concerned area. Furthermore, the instant compositions may be applied to the scalp and/or hair by spraying. After evaporation, an elastic film is formed onto the treated surface and provides continuous delivery of the actives to the scalp and/or the hair for many hours or even for days.

The compositions according to the present invention may contain one or more active agents selected from 5-alpha reductase inhibitors, antiandrogenic hormones, potassium channel agonists, amino acids, plant extracts, antioxidants, and are suitable to prevent and to treat hair loss, baldness and alopecia. The compositions prepared according to the present invention containing one or more active agents may be applied to nourish, volumize and reinforce the hair.

Examples of 5-alpha reductase inhibitors which may be included in the composition in accordance with the present invention include finasteride, dutasteride, azelaic acid, beta-sitosterol, zinc, and Vitamin B6.

Examples of antiandrogenic hormones which may be included in the composition in accordance with the present invention include spironolactone, ciproterone acetate, flutamide, ketoconazole, estrogens and their salts.

Examples of potassium channel agonists which may be included in the composition in accordance with the present invention include minoxidil.

Examples of amino acids which may be included in the composition in accordance with the present invention include L-cysteine, N-acetylcysteine, L-cosine, L-methionine, dimethylsulphone, and L-taurine.

Examples of plant species which extracts may be included in the composition in accordance with the present invention include *Serenoa repens, Aloe vera, Equisetum arvense, Panicum miliaceum, Pygeum africanum, Urtica dioica, Coix lachrymal-jobi*, and *Eriobotrya japonica*.

Examples of antioxidants which may be included in the composition in accordance with the present invention include ascorbic acid; glutathione; melatonin; tocopherols and tocotrienols; polyphenolic antioxidants including resveratrol and flavonoids; viniferols; and carotenoids including lycopene, carotenes.

Compositions of the instant invention may also contain penetration modifying systems, including absorption enhancers, or modified delivery systems, which modify the penetration rate of the actives into the epidermis and create a reservoir at the dermal-epidermal junction, to provide an increased and longer lasting availability of the active at the hair follicles. Examples of the absorption enhancers which may be included in the composition in accordance with the present invention include TRANSCUTOL® P (Diethylene glycol monoethyl ether). Examples of modified delivery systems which may be included in the composition in accordance with the present invention include microcapsules.

The pharmaceutical compositions and the methods of the present invention will now be more fully described by the following examples. It should, however, be noted that such examples are given by way of illustration and not of limitation.

EXAMPLE 1

A film forming solution having the following composition wt./wt. % was prepared:

| | |
|---|---|
| 1) Finasteride | 0.25% |
| 2) Ethyl Alcohol 96° | 55.00% |
| 3) Propylene Glycol | 5.00% |
| 4) Hydroxypropyl Chitosan | 1.00% |
| 5) Purified water | 38.75% |

Preparation

Ethyl Alcohol, Propylene Glycol and water were mixed at room temperature. Finasteride was then added and mixed until a clear solution was obtained. Hydroxypropyl Chitosan was added as the final ingredient, and the mixture was stirred at room temperature for 24 hours or until dissolution.

The obtained formulation was a clear and colorless solution, homogenous in appearance even after prolonged storage. Moreover, the liquid was able to form a matte, non-sticky and elastic film, which could strongly adhere to the scalp surface.

EXAMPLE 2

A liquid formulation having the following w/w % composition was prepared:

| | |
|---|---|
| 1) Dutasteride | 0.25% |
| 2) Ethyl Alcohol 96° | 55.00% |
| 3) Propylene Glycol | 5.00% |
| 4) Hydroxypropyl Chitosan | 2.00% |
| 5) Purified water | 37.75% |

Preparation

The formulation was prepared by using the same method described for Example 1.

Hydroxypropyl Chitosan was added as the final ingredient, and the mixture was stirred at room temperature for 24 hours or until dissolution.

The obtained formulation was a clear and colorless solution, homogenous in appearance even after prolonged storage. Moreover, the liquid was able to form a matte, non-sticky and elastic film, which could strongly adhere to the scalp surface.

EXAMPLE 3

A liquid formulation having the following w/w % composition was prepared:

| | |
|---|---|
| 1) Minoxidil | 2.00% |
| 2) Ethyl Alcohol 96° | 55.00% |
| 3) Propylene Glycol | 5.00% |
| 4) Hydroxypropyl Chitosan | 1.00% |
| 5) Purified water | 37.00% |

Preparation

The formulation was prepared by using the same method described for Example 1.

Hydroxypropyl Chitosan was added as the final ingredient, and the mixture was stirred at room temperature for 24 hours or until dissolution.

The obtained formulation was a clear and colorless solution, homogenous in appearance even after prolonged storage. Moreover, the liquid was able to form a matte, non-sticky and elastic film, which could strongly adhere to the scalp surface.

EXAMPLE 4

A liquid formulation having the following w/w % composition was prepared:

| | |
|---|---|
| 1) Spironolactone | 1.00% |
| 2) Ethyl Alcohol 96° | 55.00% |
| 3) Propylene Glycol | 5.00% |
| 4) Hydroxypropyl Chitosan | 2.00% |
| 5) Purified water | 37.00% |

Preparation

The formulation was prepared by using the same method described for Example 1.

Hydroxypropyl Chitosan was added as the final ingredient, and the mixture was stirred at room temperature for 24 hours or until dissolution.

The obtained formulation was a clear and colorless solution, homogenous in appearance even after prolonged storage. Moreover, the liquid was able to form a matte, non-sticky and elastic film, which could strongly adhere to the scalp surface.

EXAMPLE 5

An in vitro permeation test was performed by applying the film forming solution according to the Example 1 to excised hairless rat skin, obtained from dorsal or abdominal skin of male hairless rats. Portions of the skin (ca 9 cm$^2$), after removal of adhering fat and subcutaneous tissues, were placed as a barrier between the two compartment of Gummer permeation vertical cells (Gummer, C. L. et al. The skin penetration cell: design update. Int. J. Pharm. 1987, 40, 101-104). The receiving phase was introduced into the lower compartment and 1.0 or 0.5 mL of the composition according to the Example 1 were regularly distributed on the exposed skin surface. At predetermined time intervals (2, 4, 8, 12, 16, 20 and 24 hours) 5.0 mL of the receiving solution were collected for analysis and immediately replaced by an equal volume of fresh buffer. The experiment was replicated 3 times.

The finasteride permeated through hairless rat skin in the 3 experiments is reported in FIG. 1. The total percent quantity (Q%) permeated through the rat hairless skin was 6.59±1.90% for the 1.0 mL dose and 8.78±1.33% for the 0.5 mL dose.

It is concluded that after the application of the film forming solution of hydroxypropyl chitosan according to Example 1, finasteride was able to permeate the rat skin rapidly and that the penetration of finasteride is long lasting.

EXAMPLE 6

A preparation having the following composition wt./wt. % was prepared:

| | |
|---|---|
| 1. finasteride | 0.25% |
| 2. purified water | 19.25% |
| 3. propylene glycol | 10.00% |
| 4. isopropanol | 70.00% |
| 5. chitosan | 0.50% |

Preparation

The formulation was prepared by dissolving chitosan and finasteride in propylene glycol, then adding the other ingredients, and stirring the mixture until dissolution. The resulting liquid was able to form an elastic film which could strongly adhere to the skin surface.

EXAMPLE 7

A liquid formulation having the following w/w % composition was prepared:

| | |
|---|---|
| 1. *Eriobotrya japonica* Leaf 1,3-butylene glycol extract[1] | 10.00% |
| 2. Ethyl Alcohol 96° | 36.50% |
| 3. Diethylene glycol monoethyl ether[2] | 0.50% |
| 4. Hydroxypropyl Chitosan | 1.00% |
| 5. Purified water | 52.00% |

[1]Loquat Leaf Extract CA;
[2]TRANSCUTOL ® P

Preparation

Ethyl Alcohol and water were mixed at room temperature. The Loquat Leaf Extract CA was then added and mixed until a clear solution was obtained. Diethylene glycol monoethyl ether was added, Hydroxypropyl Chitosan was added as the final ingredient, and the mixture was stirred at room temperature for 4 hours or until dissolution.

The obtained formulation was a clear and colorless solution, homogenous in appearance. Moreover, the liquid was able to form a matte, non-sticky and elastic film.

EXAMPLE 8

A liquid formulation having the following w/w % composition was prepared:

| | |
|---|---|
| 1. *Coix lachrymal-jobi* 1,3-butylene glycol solution[1] | 10.00% |
| 2. Ethyl Alcohol 96° | 36.50% |
| 3. Diethylene glycol monoethyl ether[1] | 0.50% |
| 4. Hydroxypropyl Chitosan | 1.00% |
| 5. Purified water | 52.00% |

[1]Hydrolyzed *Coix* Extract;
[2]TRANSCUTOL ® P

Preparation

Ethyl Alcohol and water were mixed at room temperature. The Hydrolyzed Coix Extract was then added and mixed until a clear solution was obtained. Diethylene glycol monoethyl ether was added, Hydroxypropyl Chitosan was added as the final ingredient, and the mixture was stirred at room temperature for 4 hours or until dissolution.

The obtained formulation was a clear and slightly yellow solution, homogenous in appearance. Moreover, the liquid was able to form a matte, non-sticky and elastic film.

EXAMPLE 9

A liquid formulation having the following w/w % composition was prepared:

| | |
|---|---|
| 1) *Eriobotrya japonica* Leaf 1,3-butylene glycol extract[1] | 10.00% |
| 2) Ethyl Alcohol 96° | 36.50% |
| 3) Diethylene glycol monoethyl ether[2] | 0.50% |
| 4) Chitosan | 1.00% |
| 5) Purified water | 52.00% |

[1]Loquat Leaf Extract CA;
[2]TRANSCUTOL ® P

Preparation

Chitosan was dissolved in water after acidification with acetic acid at pH 3.0. Then, ethyl alcohol was added and the mix was stirred till to obtain a clear viscous solution. At this point, the pH rose to pH 5.5.

Diethylene glycol monoethyl ether was added and then the herbal extract was added. The obtained formulation was a clear and colorless solution, homogenous in appearance and slightly viscous.

EXAMPLE 10

An open, comparative test was performed to assess the effect of the solution according to the Example 9 on the hair of 4 healthy female volunteers, aged 20-45 years, who gave their informed consent. All the women had smooth hair, subject 1 had hair which was natural, subjects 2 and 3 had hair which was dyed, subject 4 had hair with streaks. After washing the hair with a standard shampoo, two wisps were sampled from each woman, from the same area of the scalp.

The following procedures were followed:

A solution according to the Example 9 was applied to one wisp of hair from each woman and then blow-dried. The other wisp was blow-dried and served as untreated control.

The following parameters were measured:

1. Volume: 0=scarce, 1=poor, 2=moderate, 3=high volume
2. Resistance to traction (as per the UNI EN ISO2062: 1997)
3. Spectrophotometry (shining was measured according to the CIE, Commission Internationale de l'Eclairage)
4. Digital 3D videomicroscopy by 3D Hirox KH-770at 2100× and 350×

The results are as follows: the treated wisps resulted in a 12% higher mean volume; a 6% higher shining as measured by spectrophotometry; and 11% higher resistance to traction, when compared to the control wisps. Using digital videomicroscopy, the treated hairs appeared smoother with a more regular aspect of the cuticle.

In conclusion, the preparation as per Example 9 was able to volumize the human hair, to reinforce the hair and to improve shining and smoothness of the hair.

EXAMPLE 11

A liquid formulation having the following w/w % composition was prepared:

| | |
|---|---|
| 1) L-methionine | 2.00% |
| 2) Ethyl Alcohol 96° | 36.00% |
| 3) Diethylene glycol monoethyl ether[1] | 0.50% |
| 4) Lactic acid | 0.50% |
| 5) Chitosan | 1.00% |
| 6) Purified water | 60.00% |

[1]TRANSCUTOL ® P

Preparation

The composition was prepared by using a method similar to that of Example 9, acidifying with lactic acid to dissolve chitosan in water, and adding methionine as the last step.

EXAMPLE 12

A liquid formulation having the following w/w % composition was prepared:

| | |
|---|---|
| 1) Resveratrol | 2.00% |
| 2) Ethyl Alcohol 96° | 55.00% |
| 3) Propylene Glycol | 5.00% |
| 4) Hydroxypropyl Chitosan | 1.00% |
| 5) Purified water | 37.00% |

The formulation was prepared by using the same method described for Example 1. Hydroxypropyl Chitosan was added as the final ingredient, and the mixture was stirred at room temperature for 24 hours or until dissolution.

The obtained formulation was a clear solution, homogenous in appearance even after prolonged storage. Moreover, the liquid was able to form a matte, non-sticky and elastic film, which could strongly adhere to the scalp surface.

EXAMPLE 13

An open, comparative test was performed to assess the effect of the solutions according to Examples 11 and 12 on the hair of 5 healthy female volunteers, aged 30-47 years, who gave their informed consent. All the women had smooth hair. After washing the hair with a standard shampoo, three wisps were sampled from each woman, from the same area of the scalp, and the following procedures were followed:

The solution according to Example 11 was applied to one wisp of hair from each woman. The solution according to Example 12 was applied to a second wisp of hair from each woman. Each wisp of hair was blow-dried after treatment. The third wisp of hair was blow-dried and served as an untreated control.

The following parameters were measured:
1) Volume: 0=scarce, 1=poor, 2=moderate, 3=high volume
2) Shining, measured by spectrophotometry according to the CIE, Commission Internationale de l'Eclairage)

The results were as follows: the wisps treated with the composition according to Example 11 resulted in a 15% higher mean volume and an 11% higher shining as measured by spectrophotometry, when compared to the untreated control wisps.

The wisps treated with the composition according to the Example 12 resulted in an 18% higher mean volume and an 8% higher shining as measured by spectrophotometry, when compared to untreated control wisps.

In conclusion, the compositions as per Examples 11 and 12 were able to volumize the human hair and to improve the shining of the hair.

The invention claimed is:

1. A method for the treatment of scalp conditions, hair conditions and/or hair diseases consisting essentially of applying to the scalp and/or hair of a human being, a therapeutically effective amount of a composition consisting essentially of
    (a) hydroxypropyl chitosan;
    (b) finasteride and
    (c) a lower alkanol.

2. The method of claim 1, wherein component (a) is present in an amount of from 0.1 to 10 wt. % of the composition.

3. The method of claim 2, wherein component (a) is present in an amount of from 0.2 to 5 wt. % of the composition.

4. The method of claim 3, wherein component (a) is present in an amount of from 0.25 to 2.0 wt. % of the composition.

5. The method of claim 1, wherein component (b) is present in an amount of from 0.001 to 25 wt. % of the composition.

6. The method of claim 5, wherein component (b) is present in an amount of from 0.2 to 10 wt. % of the composition.

7. The method of claim 6, wherein component (b) is present in an amount of from 0.4 to 5.0 wt. % of the composition.

8. The method of claim 1, wherein component (c) is present in an amount of from 25% to 90 wt. % of the composition.

9. The method of claim 8, wherein component (c) is present in an amount of from 30% to 85 wt. % of the composition.

10. The method of claim 9, wherein component (c) is present in an amount of from 35% to 80 wt. % of the composition.

11. The method of claim 1, wherein the lower alkanol is selected from the group consisting of ethanol and isopropanol.

12. The method of claim 1, wherein the composition is in a form selected from the group consisting of a microcapsule, solution, emulsion, suspension and colloid.

13. The method of claim 1, wherein the composition is applied by spraying.

14. The method of claim 1, wherein the scalp conditions, hair conditions and/or diseases are selected from the group consisting of hair loss, baldness, alopecia, androgenetic alopecia and hair fragility.

15. A method for the treatment of scalp conditions, hair conditions and/or hair diseases consisting essentially of applying to the scalp and/or hair of a human being, a therapeutically effective amount of a composition consisting essentially of
    (a) hydroxypropyl chitosan;
    (b) finasteride;
    (c) a lower alkanol; and
    (d) diethylene glycol monoethyl ether.

16. The method of claim 15, wherein component (a) is present in an amount of from 0.1 to 10 wt. % of the composition.

17. The method of claim 16, wherein component (a) is present in an amount of from 0.2 to 5 wt. % of the composition.

18. The method of claim 17, wherein component (a) is present in an amount of from 0.25 to 2.0 wt. % of the composition.

19. The method of claim 15, wherein component (b) is present in an amount of from 0.001 to 25 wt. % of the composition.

20. The method of claim 19, wherein component (b) is present in an amount of from 0.2 to 10 wt. % of the composition.

21. The method of claim 20, wherein component (b) is present in an amount of from 0.4 to 5.0 wt. % of the composition.

22. The method of claim 15, wherein component (c) is present in an amount of from 25% to 90 wt. % of the composition.

23. The method of claim 22, wherein component (c) is present in an amount of from 30% to 85 wt. % of the composition.

24. The method of claim 23, wherein component (c) is present in an amount of from 35% to 80 wt. % of the composition.

25. The method of claim 15, wherein the lower alkanol is selected from the group consisting of ethanol and isopropanol.

26. The method of claim 15, wherein the composition is in a form selected from the group consisting of a microcapsule, solution, emulsion, suspension and colloid.

27. The method of claim 15, wherein the composition is applied by spraying.

28. The method of claim 15, wherein the scalp conditions, hair conditions and/or diseases are selected from the group consisting of hair loss, baldness, alopecia, androgenetic alopecia and hair fragility.

* * * * *